United States Patent
Porter

(10) Patent No.: US 8,580,120 B2
(45) Date of Patent: Nov. 12, 2013

(54) REDUCTION IN FLUSHING VOLUME IN AN ADSORPTIVE SEPARATION SYSTEM

(75) Inventor: John R. Porter, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 59 days.

(21) Appl. No.: 13/425,090

(22) Filed: Mar. 20, 2012

(65) Prior Publication Data

US 2012/0241384 A1  Sep. 27, 2012

Related U.S. Application Data

(60) Provisional application No. 61/466,694, filed on Mar. 23, 2011.

(51) Int. Cl.
*B01J 49/00* (2006.01)
*C07C 7/12* (2006.01)

(52) U.S. Cl.
USPC ........... 210/670; 585/820; 585/826; 585/827; 585/828; 585/829; 585/830

(58) Field of Classification Search
USPC ............. 585/820, 826, 827, 828, 829, 830; 210/670
See application file for complete search history.

(56) References Cited

U.S. PATENT DOCUMENTS

| | | | |
|---|---|---|---|
| 3,040,777 A | 6/1962 | Carson et al. | |
| 3,201,491 A | 8/1965 | Stine et al. | |
| 3,422,848 A | 1/1969 | Liebman et al. | |
| 3,706,812 A | 12/1972 | Derosset et al. | |
| 3,761,533 A | 9/1973 | Otani et al. | |
| 4,029,717 A | 6/1977 | Healy et al. | |
| 4,031,156 A | 6/1977 | Geissler et al. | |
| 5,750,820 A * | 5/1998 | Wei .............................. | 585/826 |
| 7,208,651 B2 | 4/2007 | Frey | |
| 7,396,973 B1 | 7/2008 | Winter | |
| 7,977,526 B2 | 7/2011 | Porter | |
| 8,008,536 B2 | 8/2011 | Winter et al. | |
| 2010/0125163 A1 | 5/2010 | Porter et al. | |
| 2010/0305381 A1 | 12/2010 | Go et al. | |
| 2011/0245573 A1 | 10/2011 | Porter et al. | |

FOREIGN PATENT DOCUMENTS

| | | |
|---|---|---|
| EP | 0 787 517 | 8/1997 |
| WO | WO 95/07740 | 3/1995 |
| WO | WO 2010/138284 | 12/2010 |

* cited by examiner

*Primary Examiner* — In Suk Bullock
*Assistant Examiner* — Philip Louie
(74) *Attorney, Agent, or Firm* — Andrew B. Griffis

(57) ABSTRACT

A process for separating a product from a multicomponent feedstream to an adsorption apparatus or system is described. The apparatus or system may comprise a moving-bed or a simulated moving-bed adsorption means. The product comprises at least one organic compound, such as an aryl compound with alkyl substitutes. In embodiments the conduits used to supply the feedstream to the apparatus or system are flushed with media of multiple grades. The improvement is a more efficient use of the desorbent. In embodiments the process achieves improvements in one or more of efficiency of adsorption separation, capacity of adsorption apparatus systems, and purity of product attainable by adsorption process.

6 Claims, 4 Drawing Sheets

REDUCTION IN FLUSHING VOLUME IN AN ADSORPTIVE SEPARATION SYSTEM

PRIORITY CLAIM

This application claims the benefit of and priority to U.S. Patent Application Ser. No. 61/466,694, filed Mar. 23, 2011, which is incorporated by reference herein in its entirety.

FIELD OF THE INVENTION

The invention relates to a process for separating one or more of the components from two or more multicomponent fluid mixtures, and more particularly to a process for separating organic compounds from such a fluid mixture by means of adsorption apparatus, such as moving-bed or simulated moving-bed adsorption apparatus, and a system comprising such apparatus.

BACKGROUND OF THE INVENTION

Various means are currently available to separate the components of a multicomponent fluid mixture. If the densities of the components differ sufficiently, the effects of gravity over time may be adequate to separate the components. Depending on the quantities of the components involved, a centrifuge may be used to more rapidly separate components with different densities. Alternatively, distillation may be used to separate components with different boiling points.

Some fluid mixtures comprise components which have similar boiling points, and in such cases, separation by distillation may be a difficult and an inefficient means to separate these components. Too many contaminants, e.g., unwanted components, also may evaporate along with (or fail to evaporate from) the desired component(s), or the separation may require high energy expenditures due to the recycling through the distillation process that may be necessary to attain a desired degree of separation or purity.

In view of these and other deficiencies of these aforementioned processes, adsorption often has been preferred as a process for separating the components from a multicomponent fluid mixture to obtain relatively pure products.

The efficiency of an adsorption process may be partially dependent upon the amount of the surface area of the adsorbent solids which is available for contact with a fluid mixture. The surface area available may be more than just the superficial, external surface of the solids. Suitable solids also may have internal spaces. Such internal spaces may comprise pores, channels, or holes in the surface of the solids and may run throughout the solids, much as in sponges. Thus, the fluid contacts not only the superficial surface, but penetrates into the solids. Sieve chambers increase the contact surface between the fluid and the solids in an adsorption process by concentrating them in a confined space. Such structures often are described as molecular sieves, and the volumetric amount of components that may be adsorbed by a molecular sieve is termed the molecular sieve capacity.

In an adsorption process, separation of the fluid components may be accomplished because the absorbent solid material may have a physical attraction for one or more of the components of the mixture in preference to other components of the mixture. Although all of the components of a mixture may be attracted in varying degrees to the material, there is a preference engineered into the process, such that predominantly the desired component(s) may be attracted and remain with the material in preference over all others. Therefore, even if less preferred components of a mixture initially come into contact with a portion of the material, because of the stronger attraction of the material for the desired component(s) of the mixture, the less preferred component(s) may be displaced from the material by the desired, and more strongly preferred, component(s). Although the fluid mixture entering a sieve chamber might be composed of multiple components, the fluid mixture initially leaving the vessel would be composed largely of the components which had been less preferentially adsorbed into the material.

In adsorption processes using adsorbent solids, separation of the fluid components occurs for a period of time, but eventually all the available surface sites on and in the solids are taken up by the desired component(s) or are blocked by concentrations of unwanted components. At that point, little significant additional adsorption of component(s) from the mixture is likely to occur, and the fluid mixture which might be withdrawn from the chamber may be insignificantly changed by further exposure to the solids. The adsorption step of the process is thus ended, and the component(s) which have been adsorbed by the solids can then be removed from the solids, so as to effect separation and permit reuse of the solids.

A suitable adsorption apparatus or system might first permit adsorption of a product comprising the desired component(s) by the solids and later treat the solids to cause them to release the product and permit recovery of this product. Such an adsorption apparatus or system might comprise a "moving-bed" which permits movement of a tray or bed of the solids through a chamber, such that at different locations, the solid is subjected to different steps of an adsorption process, e.g., adsorption, purification, and desorption. These steps will be understood more clearly by the description below. Nevertheless, moving the solids through an adsorption apparatus may be difficult and involve complex machinery to move trays or beds. It also may result in loss of the solids by attrition. To avoid these problems, some adsorption apparatus and systems have been designed to "simulate" moving the tray(s) or bed(s) to the locations, e.g., zones, of different steps of an adsorption process. Simulation of the movement of the tray(s) or bed(s) may be accomplished by use of a system of conduits which permits directing and redirecting the streams of fluids into the chamber at different zones at different times. As these stream changes occur, the solids are employed in different steps in an adsorption process as though the solids were moving through the chamber.

The different zones within an adsorption apparatus or system are defined by the particular step of the adsorption process performed within each zone, e.g., (1) an adsorption step in the adsorption zone; (2) a purification step in the purification zone; (3) a desorption step in the desorption zone.

Adsorption Zone: when a multicomponent fluid feedstream, such as a feedstream comprising the C8 aromatic hydrocarbons orthoxylene (OX), metaxylene (MX), paraxylene (PX), and ethylbenzene (EB), is fed into the adsorption apparatus or system, the portion of the apparatus or system into which the feedstream is being fed is termed an "adsorption zone." In the adsorption zone, the fluid comes into contact with the adsorbent material, and the desired component(s) are adsorbed by the adsorbent material. Typically, and by way of example, it is desired that paraxylene be adsorbed on the adsorbent material preferentially to the other C8 aromatic hydrocarbons. As noted above, other components may also be adsorbed, but preferably to a lesser extent. This preferential adsorption may be achieved by the selection of an adsorbent material, e.g., adsorbent solids, which have a preference for adsorbing the desired component(s) from the multicomponent feedstream. Such materials are well-known in the art and commercially available. Although only the desired component(s) may have been adsorbed by the solids, other less preferentially adsorbed components of the fluid mixture may still remain in void spaces between the solids and possibly, in the pores, channels, or holes within the solids. These unwanted components preferably are removed from the solids before the desired component(s) are recovered from the solids, so that they are not recovered along with the product.

Purification Zone: after adsorption, the next step is to purify the fluid and adsorbent material in the chamber. In this step, the tray(s) or bed(s) may be moved or flow within the conduits may be changed, so that the multicomponent feedstream may no longer be fed into the adsorption zone. Although the tray(s) or bed(s) have not physically moved, the material may now be described as being in a "purification zone" because a fluid stream, e.g., a purification stream, is fed into the adsorbent material to flush the unwanted components from the adsorbent material, e.g., from within and from the interstitial areas between the solids. Thus, a fluid comprising unwanted components, termed "raffinate", is flushed from the purification zone by substituting a fluid comprising the desired component(s) or other component(s) deemed to be more acceptable for the unwanted components. Such substitution of one fluid for another in the purification zone is termed a "flush" (both the act of substitution and also the material that is used to flush the unwanted components). The flush may be a relatively inert material such as paradiethylbenzene (PDEB), or in the case of paraxylene being the desired compound to be separated, the flush liquid may be a solution high enough in paraxylene concentration to make the separation process worthwhile. The unwanted components may be withdrawn in a raffinate stream. In the case where paraxylene is separated from its C8 aromatic hydrocarbon isomers, the raffinate is a paraxylene-depleted stream which may subsequently be isomerized to equilibrium paraxylene concentration by processes well-known in the art and recycled through the adsorption process.

Because an objective of the adsorption process may be to separate the product comprising the desired component(s) from other components which may have nearly the same boiling point or density as the desired component(s), purification may displace unwanted components and substitute another fluid which can be more readily separated by other means, e.g., distilled.

Desorption Zone: after the solids have been subjected to the purification stream, the stream in the conduit(s) may again be changed to introduce a desorbent stream into the chamber to release the product. The desorbent stream contains desorbent which is more preferentially adsorbed by the solids than the product comprising the desired component(s). The desorbent chosen will depend in part upon the desired component(s), the adsorbent materials, and the ease with which the desorbent can be separated from the product. Once the desorbent stream has been introduced to the chamber, the product may be withdrawn from the chamber. Withdrawn product is known as "extract".

Each and every step and zone might be present somewhere in an adsorption apparatus or system if simultaneous operations are conducted. Nevertheless, the steps may be performed successively or staggered over time. Further, in some adsorption processes, the unwanted components may be adsorbed, and the product comprising the desired component(s) allowed to pass through the adsorption apparatus or system. Therefore, the terms "raffinate" and "extract" are relative and may depend upon the particular nature of the components being separated, the preference of the solids, and the nature of the apparatus or system. Although in embodiments the present invention will be discussed primarily in terms of apparatus and systems in which the product is adsorbed by the solids, the invention is not limited to such configurations.

An apparatus suitable for accomplishing the adsorption process of this invention is a simulated moving-bed adsorption apparatus. A commercial embodiment of a simulated moving-bed adsorption apparatus is used in the well-known Parex™ Process, which is used to separate C8 aromatic isomers and provide a more highly pure paraxylene (PX) from a less highly pure mixture. See by way of example U.S. Pat. Nos. 3,201,491; 3,761,533; and 4,029,717.

Typically, such an adsorption apparatus is contained in a vertical chamber packed with adsorbent solids, possibly in trays or beds stacked within the chamber. More than one type of solid also might be used. The chamber also may have the capability to perform each of the above-described steps simultaneously within different locations, e.g., zones, in the chamber. Thus, the composition of the fluid in the chamber may vary between zones although there may be no structures completely separating these zones. This may be achieved by the use of a serially and circularly interconnected matrix of fluid communication conduits including associated valves, pumps, and so forth, which permit streams to be directed and redirected into different zones of the chamber and to change the direction of these streams through the solids within the different zones of the chamber. The different zones within the chamber may have constantly shifting boundaries as the process is performed. Any flushing of desired or undesired components into or out of any particular adsorbent bed must take into account also liquid material contained within the serially and circularly interconnect matrix of fluid communication conduits leading into or out of the bed lines.

The cyclic advancement of the streams through the solids in a simulated moving-bed adsorption apparatus may be accomplished by utilizing a manifold arrangement to cause the fluid to flow in a counter current manner with respect to the solids. The valves in the manifold may be operated in a sequential manner to effect the shifting of the streams in the same direction as overall fluid flow throughout the adsorbent solids. In this regard see U.S. Pat. No. 3,706,812. Another means for producing a countercurrent flow in the solid adsorbent is a rotating disc valve by which the streams, e.g., feed, extract, desorbent, raffinate, and line flush, are advanced cyclically in the same direction through the adsorbent solids. Both U.S. Pat. Nos. 3,040,777 and 3,422,848 disclose suitable rotary valves. Both suitable manifold arrangements and disc valves are known in the art. More recently, a system has been described using dual rotary valves. See U.S. application Ser. No. 12/604,836, now allowed.

Normally there are at least four streams (feed, desorbent, extract, and raffinate) employed in the procedure. The location at which the feed and desorbent streams enter the chamber and the extract and raffinate streams leave the chamber are simultaneously shifted in the same direction at set intervals. Each shift in location of these transfer points delivers or removes liquid from a different bed within the chamber. In many instances, one zone may contain a larger quantity of adsorbent material than other zones. Moreover, zones other than those discussed above may also be present. For example, in some configurations, a buffer zone between the adsorption zone and the desorption zone may be present and contain a small amount of adsorbent material relative to the zones surrounding it. Further, if a desorbent is used that can easily desorb extract from the adsorbent material, only a small amount of the material need be present in the desorption zone in comparison to the other zones. In addition, the adsorbent need not be located in a single chamber, but may be located in multiple chambers or a series of chambers.

Introducing and withdrawing fluids to the beds may comprise a plurality of fluid communication conduits, and the same fluid communication conduit may be used in a first instance to input a feedstream into the apparatus or system and later to withdraw an extract stream. This can result in reduced product purity due to contamination of the withdrawn product. Fluid communication conduits may contain unwanted components, such as residue remaining in the conduit from earlier additions or withdrawals of streams. This problem may be overcome by employing separate conduits for each stream or by removing such residue from the conduits by flushing them with a medium which would not effect product purity as adversely as would an unwanted component remaining in the fluid communication conduit. A preferred flushing medium has been the product or the desorbent, which might be more readily separated downstream of the chamber than would the residue. See U.S. Pat. No. 4,031,156. Nevertheless, flushing conduits with the product reduces the output of the adsorption process.

A standard Parex™ unit for separating paraxylene (PX) from the other C8 aromatic isomers, metaxylene (MX), orthoxylene (OX), and ethylbenzene (EB), has a single feed to a single rotary valve or parallel rotary valves. The rotary valve directs the feed to a bed line, which (viewed schematically, such as in the attendant drawings described herein) is somewhere between the extract (which may comprise, by way of example, 99.7% paraxylene (PX) and desorbent) and the raffinate (PX-depleted xylenes and desorbent) withdrawal points. Since the process is a simulated moving bed process, the bed lines are shared with all of the feed and product streams, and therefore the bed lines must be flushed between the feed injection point and the extract withdrawal point in order to prevent contamination of the product. A standard unit has a primary flush which removes the majority of contaminants and a secondary flush which removes trace impurities just before the extract point.

The standard commercial simulated moving bed has only a single feed inlet, various streams of different compositions are typically blended together and fed to a single point in the Parex process. However, as indicated in U.S. Pat. No. 5,750, 820 (see also U.S. Pat. No. 7,396,973), it is better to segregate feeds which are of substantially different composition, such as concentrated paraxylene from a selective toluene disproportionation unit (generally 85-90% paraxylene) and equilibrium xylenes (generally about 23% paraxylene) from a powerformer, isomerization unit or transalkylation unit. This can be done by using the primary line flush as a second feed point for the paraxylene concentrate and using the secondary flush as the sole flushing stream. Having only a single flush does result in a slight compromise in the separation process, but the compromise typically is far outweighed by the benefit of optimizing the feed location of the paraxylene concentrate as far as net purity in the final product.

There is a problem with the above configuration in that the standard Parex unit has the secondary flush located close to the extract withdrawal point in order to minimize contaminants that are withdrawn with the extract. However, when the secondary flush is very close to the extract withdrawal point and concentrated paraxylene (having associated impurities) is being flushed from the bed line, the configuration will be too close to the extract withdrawal point and the highest separation of the feed will not be realized.

This problem was recently recognized and solved by some of the present inventors. The solution is that the feed locations of both the concentrated paraxylene in the primary flush and also the location of the secondary flush are modified to realize the full benefit of the feed configuration in U.S. Pat. No. 5,750,820. By moving the secondary flush further away from the extract, the material flushed from the bed line will be injected at a more efficient location. See U.S. application Ser. No. 12/774,319. The problem and solution discussed in that application are noted in the description of FIG. 1, herein below.

Still there is the problem that too much energy is expended in purification by means of the simulated countercurrent adsorptive separation, particularly when two feeds are provided having differing concentrations of the desired product (generally PX or paraxylene). To this end, more recently, it has been recognized that the aforementioned processes can be yet still further improved by using the first flush output as the second flush input. In preferred embodiments, there is no step of purification, such as by distillation, the primary flush out material before it is used as secondary flush. See U.S. Provisional Application No. 61/319,080, filed Mar. 30, 2010. Again, this solution is noted in the description of FIG. 2, herein below.

U.S. Pat. No. 7,208,651 describes increased product purity in an adsorptive separation process by flushing the contents of the transfer line (or bed line) previously used to remove the raffinate stream away from the adsorbent chamber. This flush step eliminates the passage of a quantity of the raffinate material into the adsorbent chamber in the transfer-line flush period or when the process conduit is subsequently used to charge the feed stream to the adsorbent chamber.

Still, all of the processes are still very energy-intensive due, notwithstanding the improvements provided by the above-mentioned inventions, at least in part, to the intensive use of materials such as the desorbent, which is typically reused after purification downstream of the bed systems described above. It would be very beneficial if all of the systems described could be modified simply so that energy requirements could be still further reduced. The present inventor has realized that yet further improvements can be achieved because it has now been realized that the volume of flushes can be reduced, in embodiments at least by half the volume of flush normally used. This provides, in embodiments, at least one of an increase in the energy efficiency of the system, a decrease in the material requirements, and an increase in the purity of the product.

SUMMARY OF THE INVENTION

The invention is directed to a process for separating a product from at least one multicomponent feed by simulated countercurrent adsorptive separation in a simulated moving-bed adsorption apparatus comprising at least one rotary valve and plural sieve chambers, characterized by the steps of: (a) introducing a first multicomponent feed, comprising at least one desired product, through at least one fluid communication conduit into said apparatus; (b) withdrawing a first multicomponent extract, comprising at least one desired product, through at least one fluid communication conduit out of said apparatus; (c) flushing said at least one conduit in step (a) with at least one initial flushing medium, whereby residue of said first multicomponent feed is flushed from the at least one conduit in step (a) into said apparatus by the at least one initial flushing medium, so as to produce a first flush output comprising said at least one initial flushing medium and said residue of said first multicomponent feed; (d) flushing at least one conduit in step (b) with at least one initial flushing medium, whereby residue of said first multicomponent extract is flushed form the at least one conduit in step (b) out of said apparatus by the at least one initial flushing medium, so as to produce a first flush output comprising said at least one initial flush medium and said residue of said first multicomponent extract; (e) after step (c) flushing said at least one fluid communication conduit with a second flushing medium, with the proviso that said second flushing medium comprises said first flush output from step (d).

The invention is also directed to a process for separating a product from at least one multicomponent feed by simulated countercurrent adsorptive separation, said process comprising at least two flushing steps to improve product purity, wherein the improvement comprises: (a) the bed line containing the feed is followed directly, after said flushing steps, with product, and (b) wherein the volume of the second flush is no more than 150 vol % of the bed line volume, preferably between about 110 and 150 vol % of said bed line volume.

In preferred embodiments, there is no step of purification, such as by distillation, of the primary flush out material before it is used as secondary flush in.

In embodiments, the process comprises feeding at least two different feeds, the feeds characterized by having different concentrations of at least one product, preferably a C8 species selected from one or more isomers of xylene. It will be recognized by one of skill in the art that a continuous simulated countercurrent adsorptive separation system can have many desired end products, such as pharmaceuticals, fragrances, sugars, and the like.

In embodiments, the input location of both the primary flush and/or also the secondary flush are altered as compared with the prior art to realize the fullest benefit of the present invention.

In embodiments the conduits used to supply the feed stream to the apparatus or system are flushed with media of multiple grades.

In embodiments the process achieves improvements in one or more of efficiency of adsorption separation, capacity of adsorption apparatus systems, decrease in energy requirements (particularly in the aspects of pumping and distillation requirements), and purity of product attainable by adsorption process.

In an embodiment, the process comprises the steps of: (a) introducing a first multicomponent feed, comprising at least one desired product, through at least one fluid communication conduit into a simulated moving-bed adsorption apparatus comprising at least one rotary valve and plural sieve chambers; (b) withdrawing a first multicomponent extract, comprising at least desired product, through at least one fluid communication conduit into a simulated moving-bed apparatus comprising at least one rotary valve and plural adsorption chambers; (c) flushing the at least one conduit in step (a) with at least one initial flushing medium (which preferably comprises the at least one desired product in step (a) in an initial concentration), whereby residue of said first multicomponent feed is flushed from the at least one conduit in step (a) into the apparatus by the at least one initial flushing medium, so as to produce a primary flush out comprising said at least one initial flushing medium and said residue of said first multicomponent feed; (d) flushing the at least one conduit in step (b) with at least one initial flushing medium (which preferably comprises the at least one desired component in step (b) in an initial concentration), whereby the residue of said first multicomponent extract is flushed from the at least one conduit in step (b) out of the apparatus by the at least one initial flushing medium, so as to produce an extract flush out comprising said at least one initial flushing medium and said residue of said first multicomponent extract; (e) after step (c), flushing said at least one fluid communication conduit with a second and preferably final flushing medium, characterized in that said second flushing medium comprises said extract flush out from step (d). In preferred embodiments there is no step of distillation of said extract flush out prior to use as said second flushing medium.

In preferred embodiments, the quantity of the initial medium may not be less than that sufficient to flush the feed stream residue from the conduit.

In embodiments, the apparatus comprises plural adsorption chambers containing one or more adsorbent material selected from the group consisting of charcoal, ion-exchange resins, silica gel, activated carbon, zeolitic material, and the like, and the quantity of the initial medium may be sufficient to fill the apparatus to the sieve chamber capacity.

In embodiments, the process includes additional steps including one or more of flushing one or more conduits with a sufficient quantity of a final (or third) flushing medium comprising the at least one desired component in a final concentration, such that the final concentration is greater than the initial concentration and greater than the second concentration, and such that initial medium residue from the at least one initial medium is flushed from the conduit into the system by the final medium; withdrawing a raffinate stream from the system; introducing a desorbent stream to the system; withdrawing an extract comprised of the product and the desorbent from the system; and removing subsequently removing the product after distillation of the extract.

In yet another embodiment, the initial concentration of the at least one initial medium is continuously increased during the flushing of the at least one conduit until the initial concentration equals the final concentration. Preferably, this may be accomplished by adding the product to the at least one initial medium in gradually increasing amounts and decreasing proportionately flow from the source of the at least one initial medium; the improvement comprises using at least a portion of the first flush output as at least part of said second flushing medium.

As is well-known per se in the commercial Parex™ unit, moving the locations of liquid input and output is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and is generally from about 60 to about 90 seconds (although it can be longer or shorter). A typical process contains 24 adsorbent beds, 24 distributors located between the 24 adsorbent beds, at least two liquid input lines, at least two liquid output lines, and associated flush lines. In an embodiment of the present invention, an improvement is provided whereby the rotary valve is replumbed so that the input of the secondary flush is at least one and preferably two or more valve steps downstream of where it is, heretofore, ordinarily inputted. This is more fully illustrated by the description of FIG. 4 below. This also means that the secondary flush is added closer in sequence to the input of the primary flush, such as within three cycle steps.

It is an object of the invention to decrease pumping and distillation requirements in the purification of material utilizing a simulated moving bed adsorptive separation system.

It is another object of the invention, in one or more embodiments, to increase the efficiency of adsorption apparatus or systems, whereby contaminants, such as feed stream residue, may be removed from fluid communication conduits by flushing them from the conduits into the apparatus or system with flushing media containing concentrations of the desired component(s) of the product which are higher than that of the feed stream. It is an advantage of such embodiments that if the product is extracted through the same conduits that carried the feed stream, such as in a simulated moving-bed adsorption apparatus, extract will not be contaminated, or will have lower contamination, with feed stream residue.

It is an additional object of this invention to increase the capacity of an adsorption apparatus or system. It is an advantage of this process that excess capacity of the apparatus or system may be more fully utilized by purifying the solids with flushing media and flushing conduits with media containing the desired component(s). It is a feature of such embodiments that fluid communication conduits may be flushed with media containing concentrations of a desired component or components higher than that of the feed stream, which may be drawn from a source other than the apparatus.

It is yet another object of this invention, in embodiments, to increase the purity of the product obtained from an adsorption apparatus or system. It is a feature of embodiments of this process that contaminants may be removed from conduits and from pores, channels, and voids in adsorbent solids, and conduits may be charged with the product. It is an advantage of such embodiments that the product may be recycled through the apparatus or system, and excess apparatus or system capacity may be used to further separate other unwanted components of the feed stream remaining in the product.

It is yet still further an object of this invention to eliminate or reduce the circulation requirements of the desorbent, including downstream distillation and separation of the adsorbent from the various solutes contained therein, the solutes including the desired component (such as, in the case of xylenes, one particular isomer, which is generally paraxylene).

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

According to the invention, there is provided a process for separating a product from at least two multicomponent feeds to an adsorption apparatus or system. In an embodiment there is a simulated moving bed adsorptive separation system plumbed so that the extract flush output is connected to the secondary flush input directly, whereby the extract flush output, comprising desorbent and having a higher concentration of the desired compound as compared to the flush material prior to being used as primary flush, is then utilized as secondary flush input, resulting, in more preferred embodiments, in the secondary flush output comprising desorbent and having even higher concentration of the desired compound than in the primary flush input.

The apparatus or system may comprise a moving-bed or a simulated moving-bed adsorption means, and in embodiments provides a product comprising at least one organic compound, such as an aryl compound with alkyl substitutes, for instance (and in a preferred embodiment), paraxylene (PX). In embodiments the conduits used to supply the feed stream to the apparatus or system are flushed with media of multiple grades. In embodiments the process achieves improvements in one or more of efficiency of adsorption separation, capacity of adsorption apparatus systems, and purity of product attainable by adsorption process, while allowing for elimination or by-pass of distillation apparatus and/or pumping mechanisms.

In embodiments the feed location of both the concentrated paraxylene in the primary flush and also the location of the secondary flush are located to realize the full benefit of feed locations. In embodiments, by moving the secondary flush further away from the extract, the material flushed from the bed line will be injected into a more advantageous point in the composition profile. This allows for additional capacity or decreased use of energy associated with a decrease of desorbent recirculation will be realized.

Figure 1:
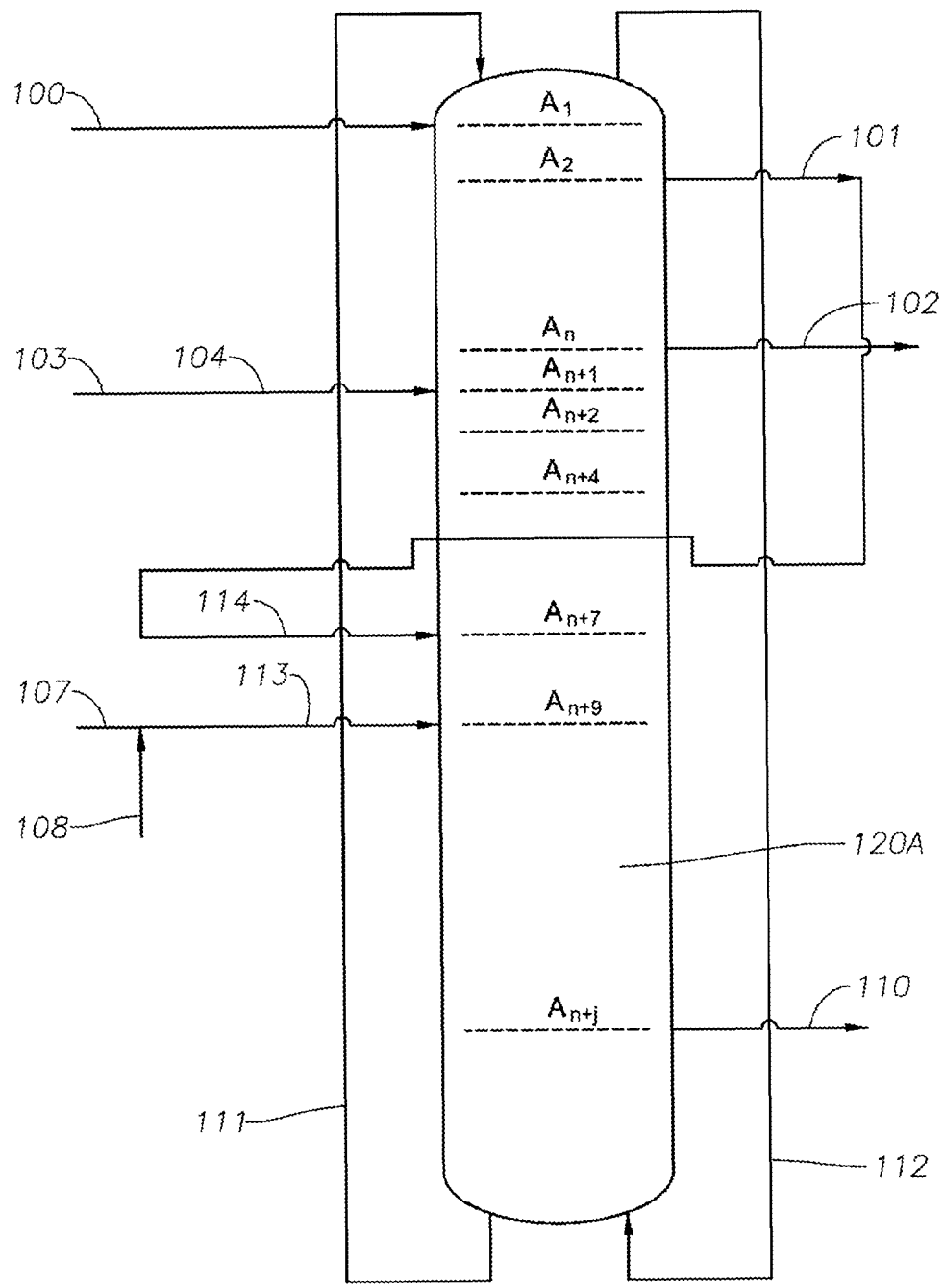
FIGS. 1-3 are schematics illustrating a prior art configurations of simulated moving bed adsorptive separation systems.

As described more fully in U.S. application Ser. No. 12/774,319, a system 120A employing a simulated countercurrent flow process such as described in U.S. Pat. Nos. 3,201,491; 3,761,533; and 4,029,717, is shown in FIG. 1, along with several modifications. The diagram in FIG. 1 will be understood by those of skill in the art to depict a simulated moving bed process. Desorbent is introduced through conduit 100, extract flush out leaves the apparatus through flush out conduit 101 and is recycled back into the system through conduit 114 as primary feed flush (containing the desired product) leaves the apparatus via conduit 102, raffinate leaves the system through conduit 110, the secondary flush is added via conduit 103, entering the system 120A through conduit 104, a first multicomponent feed is added to the system through conduit 107 and optionally a second multicomponent feed is added through line 108, as explained more fully in the following description, one or both entering the simulated moving beds through conduit 113. The first multicomponent feed typically will be a C8 aromatic hydrocarbon stream having a paraxylene concentration of approximately thermodynamic equilibrium, e.g., about 23 mol %, based on the concentration of C8 aromatic hydrocarbons, and the second multicomponent feed typically will be a C8 aromatic hydrocarbon stream having a paraxylene concentration higher than equilibrium concentration.

Not shown in the drawing, but as would be recognized by one of skilled in the art in possession of the disclosure of U.S. application Ser. No. 12/774,319, is one or more distillation towers and attendant pumps and conduits. The present inventor recognized that such downstream operations involving distillation and/or separation to purify the flush can be minimized or entirely omitted by rerouting (such as by replumbing or retrofitting) the primary flush out 101 to be used as secondary flush in 105, shown in FIG. 4, and that additional improvements can be realized by also adopting the succession of improvements shown from FIG. 1 through FIG. 3. The extract flush out 101 (all figures) has the necessary characteristics of a useful secondary flush 105 in FIG. 4, thus also avoiding at least part of the circulation of desorbent, with attendant savings in energy, equipment, while at the same time, in embodiments, providing an improved product, e.g., purified paraxylene. The embodiment of the invention shown in FIG. 4 will be discussed further below in more detail.

Continuing with the description of FIG. 1, the adsorbent represented as conduit 112 represents the upward of the adsorbent through the sieve chamber vessel 120A (accomplished by the stepping of the rotary valve) containing plural bedlines $A_1$ through $A_{n-j}$. The hydrocarbon liquid feed provided through conduit 111 flows countercurrent to the circulating adsorbent. In operation, the adsorbent does not flow, but the various feed and product streams cycle through the bed lines, represented by lines $A_1$ through $A_{n+j}$, at a rate that is different than the circulating hydrocarbon. This simulates the movement of the bed lines $A_1$ through $A_{n+j}$. Theoretically there may be any number of bed lines, thus n>2 and n+j is the maximum number of bedlines, however from a practical standpoint the number of bed lines is limited by design considerations and other factors. It will be understood that n and j are positive integers; in typical commercial embodiment the total number of bedlines is 24, and thus n+j typically will be 24. What is important is the relative positions of the bedlines caused by the stepping of the rotary valve, as would be understood by one of skill in the art. Certain bedlines, i.e., bedlines between $A_2$ and $A_n$, bedlines $A_{n+3}$, $A_{n+5}$, $A_{n+6}$, and $A_{n+10}$ through $A_{n+j-1}$ are not depicted in the figures, for convenience of view.

By way of example, in a conventional unit, the sieve preferentially starts adsorbing the paraxylene molecules from feed 113 in bedline $A_{n+9}$ and flows upward. In embodiments, the feed is selected from the group consisting of equilibrium xylenes (such as from a powerformer, isomerization unit or transalkylation unit), which is about 21-24 wt % PX, which may be provided through conduit 107, and concentrated PX streams including selective toluene disproportionation unit (STDP unit) and/or toluene alkylation with methanol, which is about 75-95 wt % PX, and admixtures thereof, which may be provided through conduit 108, the two merged in conduit 113 to enter system 120A.

The paraxylene is desorbed from the sieves in the bedlines by desorbent stream 100, the main component of which also is strongly adsorbed on the sieve(s) in bedlines $A_1$ through $A_{n+j}$, but has a different boiling point and is easily separated from the desired product(s) downstream of the apparatus. In embodiments, the desorbent is paradiethylbenzene (PDEB), toluene, or a mixture thereof, or some other strongly adsorbed compound.

The extract 102, which in the embodiment described is a mixture of the purified paraxylene and the desorbent, is withdrawn at a point between the feed 113 and the desorbent 100. The raffinate 110 consists of the paraxylene-depleted xylenes and desorbent.

Because this is a simulated moving bed process, the various feeds and products must share the lines between the bedlines (sieve beds) and rotary valve (not shown). To prevent loss of paraxylene molecules to the raffinate 110, the bed lines between the extract out 102 and desorbent in 100 are flushed out, with flush out leaving via conduit 101. The flush out in FIG. 2 can be sent to the extract tower for recovery.

In addition (and more importantly), since feed 113 is routed through the transfer lines (not shown) between the rotary valve (also not shown) and the sieve chambers $A_1$ through $A_{n+j}$ before extract 102, the transfer lines should be thoroughly flushed to avoid contamination of the product extract 102. Flush out 101 is recycle to primary flush 114 in FIG. 1 (in contrast to FIG. 2). Concentrated paraxylene product is routed through a primary flush conduit 114 and PDEB is used as secondary flush conduit 104 (or alternatively, with reference to FIGS. 3 and 4, discussed in detail below, conduit 105). The secondary flushing step through line 104 is just before the extract withdrawal location 102 in order to flush any trace amounts of contaminants that may have leaked from the sieve chamber(s) back into the bed lines.

Figure 2:
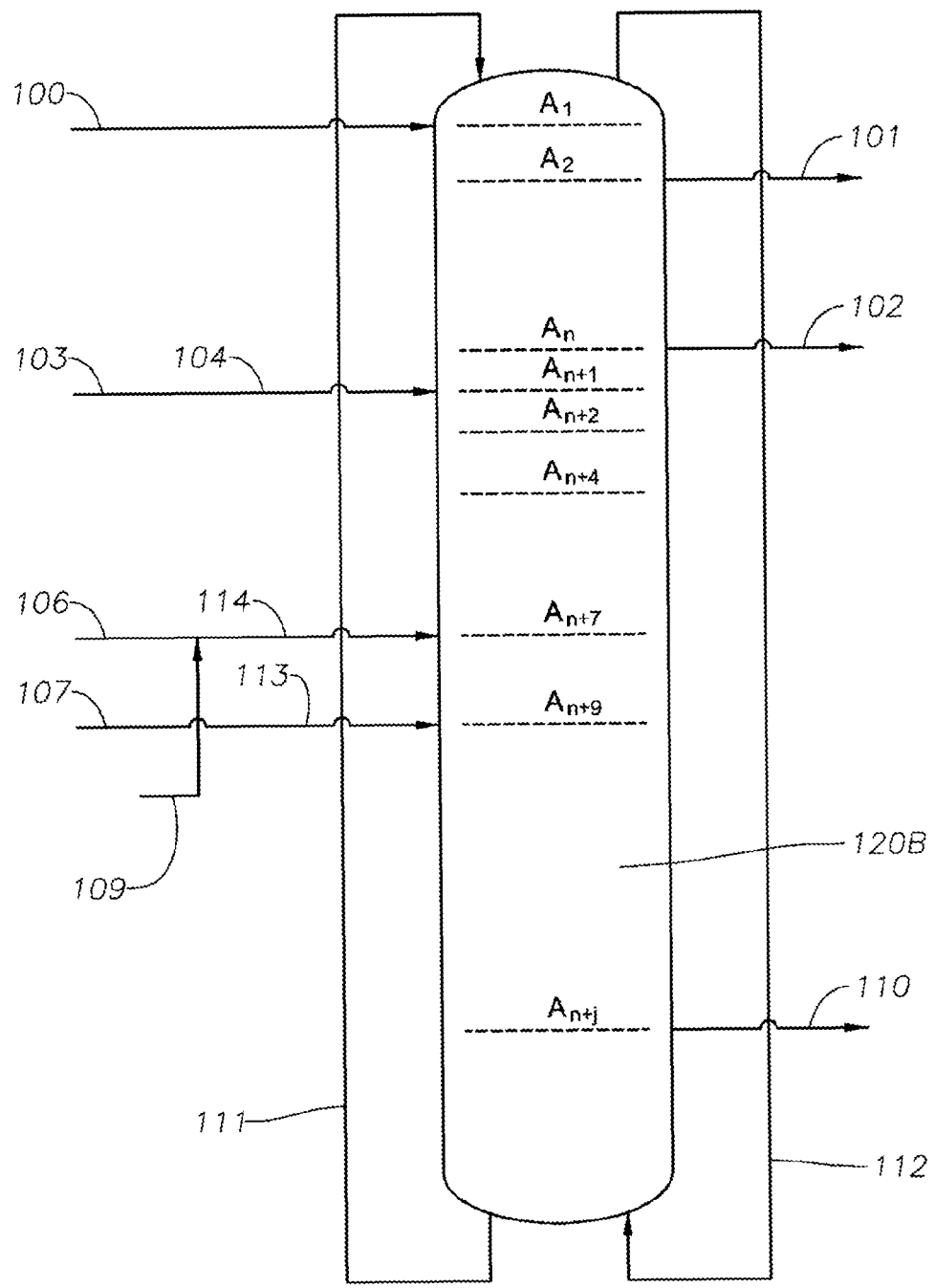

As taught in U.S. Pat. No. 5,750,820, as shown in FIG. 2, depicting simulated moving bed apparatus 120B, it is an improvement to use concentrated paraxylene, such as may be obtained downstream from conduit 102 by distillation, and route it (by one or more conduits not shown for convenience of view) through conduit 109 to conduit 114, and thus use it as primary flush 114. In contrast to merging it with fresh feed, the latter shown in FIG. 1. This step is beneficial because it routes the concentrated paraxylene into a more optimum place in the composition profile. In addition, while the concentrated paraxylene 109 is not as pure as desorbent 100 or extract flush out 101 (extract 102 is a combination of product para-xylene and desorbent, which can be separated downstream such as by distillation), it does reduce the amount of contaminants in the bed lines $A_1$ through $A_{n+j}$ and facilitate the secondary flushing step. All other features shown in FIG. 2 are as described in FIG. 1.

However, flushing a bed line (i.e., $A_1$ through $A_{n+j}$) full of concentrated PX (85-90 wt %) right next to the extract 102 creates a problem which was unanticipated and not even recognized by the inventors of the aforementioned improvement. It has been found in practice that using the aforementioned prior art teachings, the flush, in operation, may have about 10 vol % impurities whereas what is needed is closer to zero, such as 0.5 vol % or less impurities.

Figure 3:
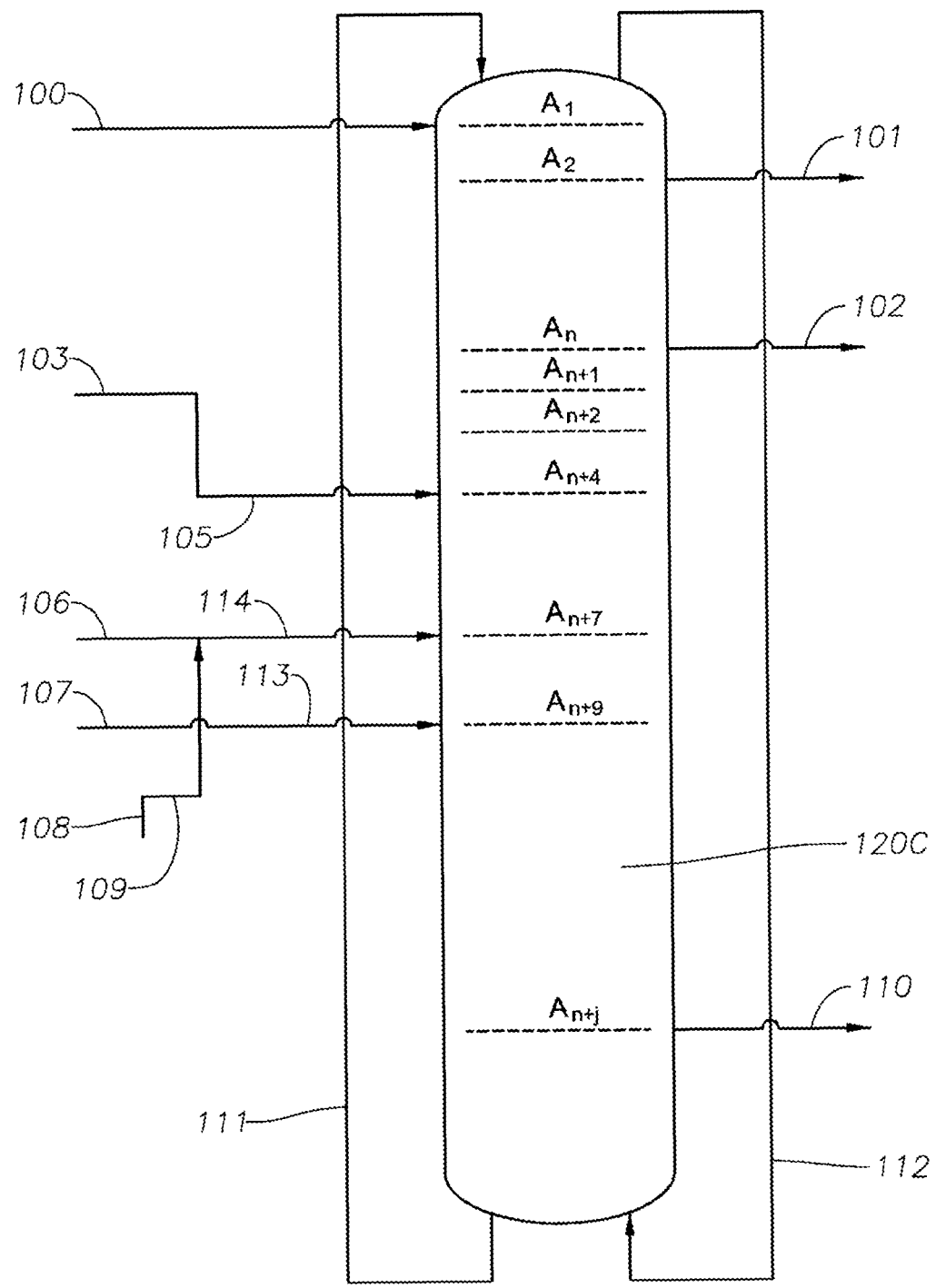

In previously mentioned U.S. application Ser. No. 12/774, 319, the inventors of that case, having discovered the aforementioned problem, proposed that in order to realize the full benefit of the movement of the input of the concentrated stream in line 108 (FIG. 1) from 107 to 114 via line 109 (compare FIGS. 1 and 2) the feed location of the secondary flush 103 must be moved to an improved place in the composition profile, e.g., further from 104, and closer to 113. One embodiment of such is depicted in FIG. 3, depicting simulated moving bed apparatus 120C, as line 105. All other features in FIG. 3 are as described in FIGS. 1 and 2.

Again, it should be emphasized, as would be known by one of skill in the art, that these positions are relative and that, although the actual positions change by virtue of the movement of the rotary valve (not shown), the relative positions of the lines remains the same. Thus, it will be understood by one of ordinary skill in the art that the figures depict a simplified simulated moving-bed apparatus with a rotary valve, wherein countercurrent "movement" of the solids in bed lines $A_1$ through $A_{n+j}$ relative to the fluid streams is simulated by the use of the rotary valve, which is not shown in the figure. As the valve rotates, the zones previously discussed move through the column in a stepwise sequence due to the change in the stream flows through the valve. In embodiments, a preferred rotary valve for performing this invention is described in U.S. Pat. No. 3,205,166. In this arrangement, each fluid communication conduit connected to the chamber may serve a different function with each step rotation of the rotary valve.

Figure 4:
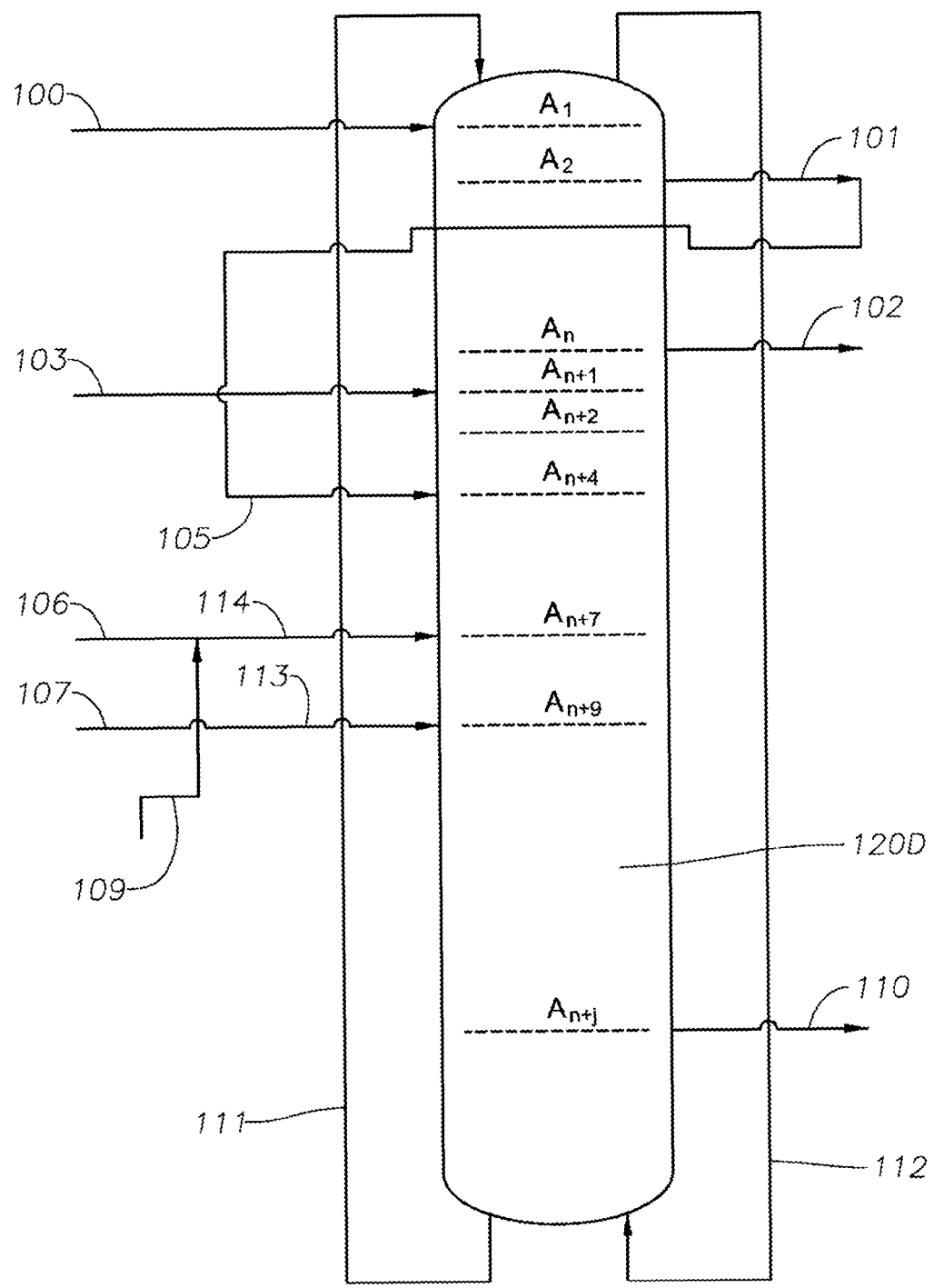
FIG. 4 is a schematic illustrating an embodiment of a separation system useful in practicing the invention.

FIG. 4 is a schematic illustrating an embodiment of the present invention. As with the previous figures, it will be understood by one of ordinary skill in the art in possession of the present disclosure that FIG. 4 depicts a simplified simulated moving-bed apparatus 120D with a rotary valve (not shown for convenience of view), wherein countercurrent "movement" of the solids in bed lines $A_1$ through $A_{n+j}$ relative to the fluid streams is simulated by the use of the rotary valve As the valve rotates, the zones previously discussed move through the column in a stepwise sequence due to the change in the stream flows through the valve. A preferred rotary valve for performing this embodiment of the present invention as shown in FIG. 4 is described in U.S. Pat. No. 3,205,166. In this arrangement, each fluid communication conduit connected to the chamber may serve a different function with each step rotation of the rotary valve.

Desorbent is introduced through conduit 100, extract flush out leaves the apparatus through conduit 101, extract (containing the desired product) leaves the apparatus via conduit 102, and raffinate leaves the system through conduit 110. Conduit 101 can be replumbed so as to connect to the conduits 104 (FIGS. 1-2) and/or 105 (FIG. 3), or, as shown in the FIG. 4, separately routed to enter system 120D through conduit 105, further down in the profile from conduit 103, to provide secondary flush.

The primary flush is added through conduit 106, entering the system 120D via conduit 114, which may instead or additionally having concentrated paraxylene added via conduit 109 (thus similar to that shown in FIGS. 2 and 3), a first multicomponent feed is added to the system through conduit 107. Optionally a second multicomponent feed may be added totally or in part through lines 109. If the second multicomponent feed (of higher Px concentration) is added in part the remainder of line 109 is mixed back with the first multicomponent feed into line 113.

The adsorbent 112 moves upward through the sieve chamber vessel 120D containing plural bedlines $A_1$ through $A_{n+j}$. The hydrocarbon liquid feed 111 flows (schematically) countercurrent to the adsorbent. In operation, the adsorbent does not flow, but the various feed and product streams cycle through the bed lines, represented by lines $A_1$ through $A_{n+j}$, at a rate that is different than the circulating hydrocarbon. This simulates the movement of the bed lines $A_1$ through $A_{n+j}$. Theoretically there may be any number of bed lines, thus n>2 and n+j is the maximum number of bedlines, however from a practical standpoint the number of bed lines is limited by design considerations and other factors. As mentioned above with respect to the previous figures, a further discussion of these details may be found in the prior art too numerous to mention, but by way of example the patents discussed in the background above and references cited therein. Again, what is important is the relative positions of the bedlines caused by the stepping of the rotary valve, as would be understood by one of skill in the art (such as that n and j are positive integers and that in typical commercial embodiments the total number of bedlines, n+j, is 24). Certain bedlines, i.e., bedlines between $A_2$ and $A_n$, bedlines $A_{n+3}$, $A_{n+5}$, $A_{n+6}$, and $A_{n+10}$ through $A_{n+j-1}$ are not depicted in FIG. 2, for convenience of view.

As in a conventional unit, the sieve preferentially starts adsorbing the paraxylene molecules from feed 107 (bedline $A_{n+9}$) and flows upward. In embodiments, the feed is selected from the group consisting of equilibrium xylenes (such as from a powerformer, isomerization unit or transalkylation unit), which is about 21-24 wt % PX, concentrated PX including material from a selective toluene disproportionation unit (STDP unit) and/or toluene alkylation with methanol, which is about 75-95 wt % PX, and admixtures thereof.

The paraxylene is desorbed from the sieves in the bedlines by desorbent stream 100, the main component of which also is strongly adsorbed on the sieve(s) in bedlines $A_1$ through $A_{n+j}$, but has a different boiling point and is easily separated from the desired product(s) downstream of the apparatus. In embodiments, the desorbent is paradiethylbenzene (PDEB), toluene, or a mixture thereof, or some other strongly adsorbed compound.

The extract 102, which in the embodiment described is a mixture of the purified paraxylene and the desorbent, is withdrawn at a point between the feed 107 and the desorbent 100. The raffinate exits conduit 110, which consist of the paraxylene-depleted (less strongly adsorbed) xylenes and desorbent.

Because this is a simulated moving bed process, the various feeds and products must share the lines between the bedlines (sieve beds) and rotary valve (not shown). To prevent loss of paraxylene molecules to the raffinate 110, the bed lines between the extract 102 and desorbent in 100 are flushed out through extract flush out in conduit 101.

Appropriately plumbed, which is within the skill of the ordinary artisan in possession of the present disclosure, the flush out can either be sent to the extract tower for recovery or recycled, used for primary flush in 106, or, as in the embodiment of the present invention (FIG. 4), used as secondary flush in through conduit 103 and/or 105. All options may be provided the operator, allowing maximum flexibility.

In addition, since feed 113 is routed through the transfer lines between the rotary valve and the sieve chambers $A_1$ through $A_{n+j}$ (none of which is shown in the figure for convenience of view but per se using conventional plumbing) before extract 102 the transfer line should be thoroughly flushed to avoid contamination of the product extract 102. Concentrated paraxylene product may still be routed through a primary flush 114 and PDEB may be used as a secondary flush 105, if desired, at predetermined times. The secondary flushing step through line 105 is just before the extract withdrawal location 102 in order to flush any trace amounts of contaminants that may have leaked from the sieve chamber(s) back into the bed lines.

As material is moved through the bed lines step by step, the bed lines must be flushed in order to avoid contamination. The bed line volume (cubic meters, gallons, etc.) divided by step time (minutes, seconds, etc.) is the volumetric flow rate (usually gpm or M3/hr) to flush out 100% of a bed line volume. However, due to the back mixing in the pipe, the flushing rate should generally be greater than 100% of the bed line volume to ensure proper flushing.

In accordance with the present invention higher purity paraxylene feed (part of which is left in the bed line between the rotary valve and the sieve chamber) requires less flushing than a lower purity feed.

Without wishing to be bound by theory, the present inventors have surprisingly discovered that not only does the improvement shown in FIG. 4 provide thermodynamic efficiency by keeping the feeds separate, less flushing is also required because the higher purity material is left in the bed line. Less flushing means lower energy consumption because less desorbent is recycled through the process.

The purity of the final product may be as high or even higher than 99.90 wt %, based on the amount of the desired component, generally paraxylene, relative to the total weight % of C8 isomers in the product.

From one point of view the evolution of the figures, beginning from FIG. 1 as the base embodiment, FIG. 2 allowed the improvement of the addition of an additional feed 109, FIG. 3 provided the movement of the secondary flush further away from the extract, and now in FIG. 4 there is the improvement of the extract flush out routed to the secondary flush input.

The invention has been described above with reference to numerous embodiments and specific examples. Many variations will suggest themselves to those skilled in this art in light of the above detailed description. Preferred embodiments of the invention include: (I) a process for separating a product from at least one multicomponent feed by simulated countercurrent adsorptive separation, comprising at least two flushing steps to increase purity of the final extract, each flushing step using a predetermined volume of flushing fluid, including a step of obtaining a first flush output and providing a second flush input, wherein the improvement comprises at least one of: (a) the bed line containing the feed is followed by said flushing steps and directly after said flushing steps, by extract; (b) the volume of fluid used for the second flush is no more than about 150 vol % of the bed line volume, preferably between about 110 and 150 vol % of said bed line volume; said process still further improved by using at least a portion of the extract flush out as at least a portion of the second flush input; and/or by being further characterized by the steps of: (a) introducing a first multicomponent feed, comprising at least one desired product, through at least one fluid communication conduit into a simulated moving-bed adsorption apparatus comprising at least one rotary valve and plural sieve chambers; (b) withdrawing a first multicomponent extract, comprising at least desired product, through at least one fluid communication conduit into a simulated moving-bed apparatus comprising at least one rotary valve and plural adsorption chambers; (c) flushing the at least one conduit in step (a) with at least one initial flushing medium (which preferably comprises the at least one desired product in step (a) in an initial concentration), whereby residue of said first multicomponent feed is flushed from the at least one conduit in step (a) into the apparatus by the at least one initial flushing medium, so as to produce said first flush output comprising said at least one initial flushing medium and said residue of said first multicomponent feed; (d) flushing the at least one conduit in step (b) with at least one initial flushing medium (which preferably comprises the at least one desired component in step (b) in an initial concentration), whereby the residue of said first multicomponent extract is flushed from the at least one conduit in step (b) out of the apparatus by the at least one initial flushing medium, so as to produce an extract flush out comprising said at least one initial flushing medium and said residue of said first multicomponent extract; (e) after step (c), flushing said at least one fluid communication conduit with a second and preferably final flushing medium, characterized in that said second flushing medium comprises said extract flush out from step (d); and/or wherein further improvement is obtained when the invention is characterized as not having a step of distillation between the step of obtaining a flush output from said extract flush out and using said extract flush out as a second flush input with an intervening step of distillation; the invention (as modified by any one or more of the aforementioned further improvement) characterized as a process for purifying a C8 aromatic hydrocarbon stream to obtain a highly concentrated solution of a single C8 aromatic isomer, particularly paraxylene, and preferably in the amount of 99.7 wt % of said single isomer, preferably paraxylene, based on the amount of total C8 aromatic hydrocarbons in said solution; and also any of the aforementioned processes further characterized by the primary flush being a solution containing paraxylene in an amount greater than 25 wt %, based on the total amount of C8 aromatic isomers in said primary flush; (II) a process for separating a product comprising paraxylene from at least one multicomponent feed comprising C8 aromatic hydrocarbons including paraxylene, orthoxylene, metaxylene, and optionally ethylbenzene by simulated countercurrent adsorptive separation, comprising at least two flushing steps, each flushing step using a predetermined volume of flushing fluid, to increase the concentration of paraxylene in said product, including a step of obtaining a first flush output and providing a second flush input, wherein the improvement comprises: (a) the bed line containing said multicomponent feed is followed directly, after said at least two flushing steps, with said product, and (b) wherein the predetermined volume of flushing fluid in each of the at least two flushing steps of the at least one multicomponent feed in said bed line is no more than about 150% of the bed line volume, preferably between about 110 and 150 vol % of said bed line volume, which may be further characterized, in a preferred embodiment, by said product comprising paraxylene in an amount of at least 99.0 vol %, preferably at least 99.5 vol %, more preferably at least 99.7 vol %, based on the total amount of C8 aromatic hydrocarbons; (III) a process for separating a product from at least one multicomponent feed by simulated countercurrent adsorptive separation in a simulated moving-bed adsorption apparatus comprising at least one rotary valve and plural sieve chambers, characterized by the steps of: (a) introducing a first multicomponent feed, comprising at least one desired product, through at least one fluid communication conduit into said apparatus; (b) withdrawing a first multicomponent extract, comprising at least one desired product, through at least one fluid communication conduit out of said apparatus; (c) flushing said at least one conduit in step (a) with at least one initial flushing medium, whereby residue of said first multicomponent feed is flushed from the at least one conduit in step (a) into said apparatus by the at least one initial flushing medium, so as to produce a first flush output comprising said at least one initial flushing medium and said residue of said first multicomponent feed; (d) flushing at least one conduit in step (b) with at least one initial flushing medium, whereby residue of said first multicomponent extract is flushed form the at least one conduit in step (b) out of said apparatus by the at least one initial flushing medium, so as to produce a first flush output comprising said at least one initial flush medium and said residue of said first multicomponent extract; (e) after step (c) flushing said at least one fluid communication conduit with a second flushing medium, with the proviso that said second flushing medium comprises said first flush output from step (d); and (IV) an apparatus adapted for carrying out any of the processes described in the aforementioned (I) or (II) or (III) and consistent schematically with FIG. 4 of this disclosure, or more specifically with reference to FIG. 4, a simulated moving bed apparatus wherein extract flush out 101 is used as secondary flush input 105. Stated another way, the apparatus is a simulated moving bed adsorption apparatus wherein the improvement comprises fluid connection from extract flush out 101 to secondary flush input 105, preferably without any intervening distillation or separation devices.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for separating a product from at least one multicomponent feed by simulated countercurrent adsorptive separation in a simulated moving-bed adsorption apparatus comprising at least one rotary valve and plural sieve chambers, characterized by the steps of: (a) introducing a first multicomponent feed, comprising at least one desired product, through at least one fluid communication conduit into said apparatus; (b) withdrawing a first multicomponent extract, comprising at least one desired product, through at least one fluid communication conduit out of said apparatus; (c) flushing said at least one conduit in step (a) with at least one initial flushing medium, whereby residue of said first multicomponent feed is flushed from the at least one conduit in step (a) into said apparatus by the at least one initial flushing medium, so as to produce a first flush output comprising said at least one initial flushing medium and said residue of said first multicomponent feed; (d) flushing at least one conduit in step (b) with at least one initial flushing medium, whereby residue of said first multicomponent extract is flushed form the at least one conduit in step (b) out of said apparatus by the at least one initial flushing medium, so as to produce a first flush output comprising said at least one initial flush medium and said residue of said first multicomponent extract; (e) after step (c) flushing said at least one fluid communication conduit with a second flushing medium, with the proviso that said second flushing medium comprises said first flush output from step (d).

2. The process of claim 1, further characterized by not having a step of distillation of said flush output before it is used as said second flushing medium.

3. The process of claim 1, wherein said final extract comprises at least 99.7 wt % paraxylene, based on the total amount of C8 aromatic hydrocarbons in said final extract.

4. The process of claim 1, wherein said first multicomponent feed has a concentration of paraxylene of greater than or equal to the thermodynamic equilibrium concentration of paraxylene in a mixture of C8 aromatic hydrocarbons.

5. The process of claim 1, wherein the initial flushing medium has a concentration of paraxylene greater than the concentration of xylene in said first multicomponent feed.

6. The process of claim 1, wherein the volume of the second flushing medium is from 110 to 150 vol % of the volume of the bedline flushed.

* * * * *